(12) United States Patent
Kawashima et al.

(10) Patent No.: US 10,675,047 B2
(45) Date of Patent: Jun. 9, 2020

(54) FORCEPS SYSTEM

(71) Applicants: National University Corporation Tokyo Medical and Dental University, Tokyo (JP); TORAY ENGINEERING CO., LTD., Tokyo (JP)

(72) Inventors: Kenji Kawashima, Tokyo (JP); Takahiro Kanno, Tokyo (JP); Ryoken Miyazaki, Tokyo (JP); Keiichi Akahoshi, Tokyo (JP); Daisuke Ban, Tokyo (JP); Minoru Tanabe, Tokyo (JP)

(73) Assignees: National University Corporation Tokyo Medical and Dental Uuniversity, Tokyo (JP); TORAY ENGINEERING CO., LTD., Tokyo (JP)

( * ) Notice: Subject to any disclaimer, the term of this patent is extended or adjusted under 35 U.S.C. 154(b) by 233 days.

(21) Appl. No.: 15/743,329

(22) PCT Filed: Jul. 12, 2016

(86) PCT No.: PCT/JP2016/070560
§ 371 (c)(1),
(2) Date: Jan. 10, 2018

(87) PCT Pub. No.: WO2017/010482
PCT Pub. Date: Jan. 19, 2017

(65) Prior Publication Data
US 2018/0199953 A1    Jul. 19, 2018

(30) Foreign Application Priority Data
Jul. 14, 2015    (JP) .................................. 2015-140409

(51) Int. Cl.
*A61B 17/29*    (2006.01)
*A61B 34/00*    (2016.01)
(Continued)

(52) U.S. Cl.
CPC .......... *A61B 17/2909* (2013.01); *A61B 17/29* (2013.01); *A61B 34/71* (2016.02);
(Continued)

(58) Field of Classification Search
CPC ......... A61B 34/00; A61B 34/30; A61B 34/37; A61B 34/70; A61B 34/71; A61B 34/74;
(Continued)

(56) References Cited

U.S. PATENT DOCUMENTS 5,649,955 A    7/1997    Hashimoto et al.
9,814,480 B2 *    11/2017    Tadano .................. A61B 34/71
(Continued)

FOREIGN PATENT DOCUMENTS

JP    H07-255735 A    10/1995
JP    2014/090800 A    5/2014
WO    2014/069003 A1    5/2014

OTHER PUBLICATIONS

International Search Report issued in PCT/JP2016/070560 dated Sep. 27, 2016 (1 page).
(Continued)

*Primary Examiner* — Tuan V Nguyen
(74) *Attorney, Agent, or Firm* — Osha Liang LLP

(57) ABSTRACT

A forceps system includes a forceps manipulator and a control unit. The forceps manipulator includes a forceps tip unit capable of bending with two degrees of freedom including a bending direction and a bending angle, a drive unit that generates a driving force for the forceps tip unit, an operation unit for instructing the bending direction and the bending angle, and a first detection unit that detects an angle (Continued)

in a rotation direction with respect to an axis of the drive transmitting unit. The control unit that controls the drive unit such that the forceps tip unit bends depending on a predetermined target bending direction and a predetermined target bending angle. The control unit sets a target bending direction on the basis of the bending direction instructed from the operation unit and the angle detected by the first detection unit.

4 Claims, 8 Drawing Sheets

(51) Int. Cl.
    *A61B 17/00*     (2006.01)
    *A61B 90/00*     (2016.01)
(52) U.S. Cl.
    CPC ....... *A61B 34/74* (2016.02); *A61B 2017/0042* (2013.01); *A61B 2017/00075* (2013.01); *A61B 2017/00323* (2013.01); *A61B 2017/00327* (2013.01); *A61B 2017/00544* (2013.01); *A61B 2017/2902* (2013.01); *A61B 2017/2905* (2013.01); *A61B 2017/2927* (2013.01); *A61B 2017/2929* (2013.01); *A61B 2034/742* (2016.02); *A61B 2090/064* (2016.02); *A61B 2090/067* (2016.02)
(58) Field of Classification Search
    CPC ......... A61B 34/75; A61B 34/77; A61B 17/29; A61B 17/2909; A61B 2017/291; A61B 2017/2905
    See application file for complete search history.

(56) References Cited

U.S. PATENT DOCUMENTS

| | | | | |
|---|---|---|---|---|
| 2005/0222587 | A1* | 10/2005 | Jinno | A61B 34/70 606/130 |
| 2014/0277107 | A1* | 9/2014 | Ishida | A61B 17/29 606/205 |
| 2015/0313619 | A1 | 11/2015 | Tadano et al. | |

OTHER PUBLICATIONS

Written Opinion of the International Searching Authority issued in PCT/JP2016/070560 dated Sep. 27, 2016 (6 pages).

\* cited by examiner

FORCEPS SYSTEM

TECHNICAL FIELD

The present invention relates to a forceps system having a forceps manipulator.

BACKGROUND ART

In the related art, a forceps manipulator has been employed as a tool for assisting a manipulation of a laparoscopic surgical operation (see Patent Document 1). The forceps manipulator is used in applications such as a work for holding an organ by bending a forceps tip unit in a human body.
Patent Document 1: Japanese Unexamined Patent Application, Publication No. 2014-090800

DISCLOSURE OF THE INVENTION

Problems to be Solved by the Invention

However, although forceps capable of realizing a more intuitive operation for an operator and accordingly shortening a surgery time or the like are demanded, the techniques of the related art including Patent Document 1 failed to sufficiently satisfy such demands.

In view of the aforementioned problems, an object of the invention is to provide forceps capable of realizing a more intuitive operation for an operator and accordingly shortening a surgery time or the like.

Means for Solving the Problems

According to an aspect of the invention, there is provided a forceps system including:
a forceps manipulator having:
a forceps tip unit capable of bending with two degrees of freedom including a bending direction and a bending angle, a drive unit that generates a driving force for the forceps tip unit;
a rod-shaped drive transmitting unit that transmits the driving force to the forceps tip unit;
an operation unit arranged at the drive unit as seen from the drive transmitting unit to instruct the bending direction and the bending angle in response to an operator's manipulation; and
a first detection unit that detects an angle in a rotation direction with respect to an axis of the drive transmitting unit; and
a control unit that controls the drive unit such that the forceps tip unit bends depending on a predetermined target bending direction and a predetermined target bending angle, wherein the control unit sets the bending angle instructed from the operation unit as a target bending angle, and
the control unit sets a target bending direction on the basis of the bending direction instructed from the operation unit and the angle detected by the first detection unit.

The forceps system further includes a second detection unit that detects an actual value of the driving force,
wherein the drive unit generates the driving force with a pneumatic pressure,
the control unit may store, in advance, a relationship between the bending direction and the bending angle of the forceps tip unit and the driving force of the forceps tip unit, control unit may obtain a target value of the driving force from the target bending direction and the target bending angle on the basis of the relationship, and
control unit may control the drive unit on the basis of the target value of the driving force and an actual value of the driving force detected by the second detection unit.

The forceps tip unit, the drive transmitting unit, and the drive unit may be configured so as to be detachable from the forceps manipulator.

The forceps tip unit may have a flexible joint capable of bending with two degrees of freedom including the bending direction and the bending angle.

Effects of the Invention

According to the invention, it is possible to provide forceps capable of realizing a more intuitive operation for an operator and accordingly shortening a surgery time or the like.

PREFERRED MODE FOR CARRYING OUT THE INVENTION

An embodiment of the present invention will now be described with reference to the accompanying drawings.

Figure 1:
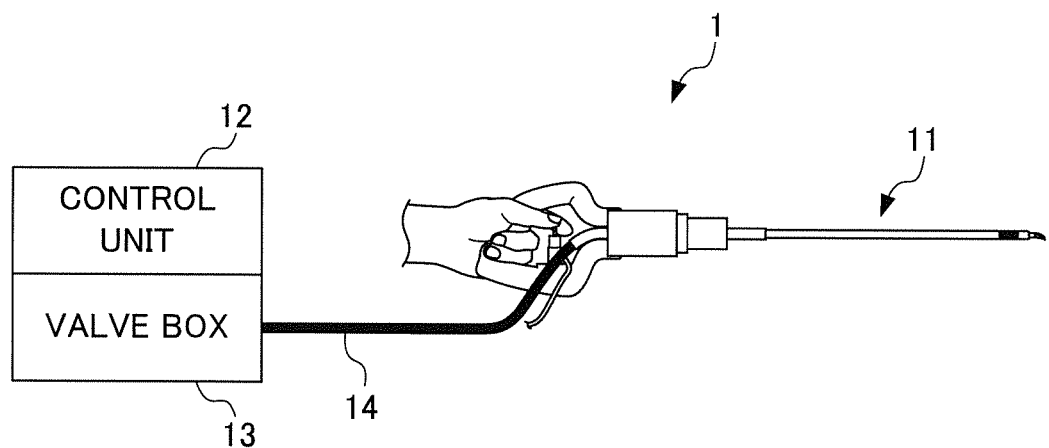
FIG. 1 is a diagram schematically illustrating an exterior configuration of a forceps system provided with a forceps manipulator according to an embodiment of the invention.

FIG. 1 is a diagram schematically illustrating an exterior configuration of a forceps system provided with a forceps manipulator according to an embodiment of the invention. The forceps system 1 according to this embodiment includes a forceps manipulator 11, a control unit 12, a valve box 13, and a pneumatic pipe 14. The forceps manipulator 11 is internally provided with a pneumatic cylinder (such as pneumatic cylinder groups 41a and 41b of FIGS. 4A and 4B and the like) to change (bending with two degrees of freedom) a posture of its tip section (the forceps tip unit 21 of FIG. 2) by driving the pneumatic cylinder. The pneumatic cylinder is driven using the air supplied from a servo valve of the valve box 13 through a pneumatic pipe 14 on the basis of the control of the control unit 12.

Figure 2:
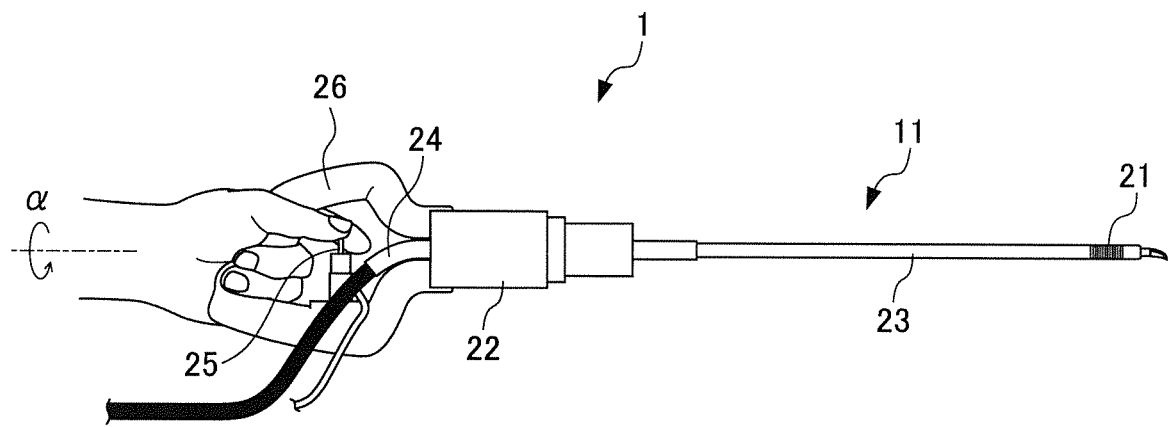
FIG. 2 is a diagram schematically illustrating an exterior configuration of the forceps manipulator according to an embodiment of the invention.

FIG. 2 is a diagram schematically illustrating an exterior configuration of the forceps manipulator according to an embodiment of the invention. The forceps manipulator 11 includes a forceps tip unit 21 capable of bending with two degrees of freedom, a drive unit 22 that generates a driving force for the forceps tip unit 21, a rod-shaped drive transmitting unit 23 that transmits the driving force to the forceps tip unit 21, a sensor section 24 that detects an angle of a rotation direction with respect to an axis of the drive transmitting unit 23, an operation unit 25 that instructs a bending operation of the forceps tip unit 21 in response to an operator's manipulation, and a holding section 26 gripped by an operator's hand to hold the forceps manipulator 11.

Figure 3:
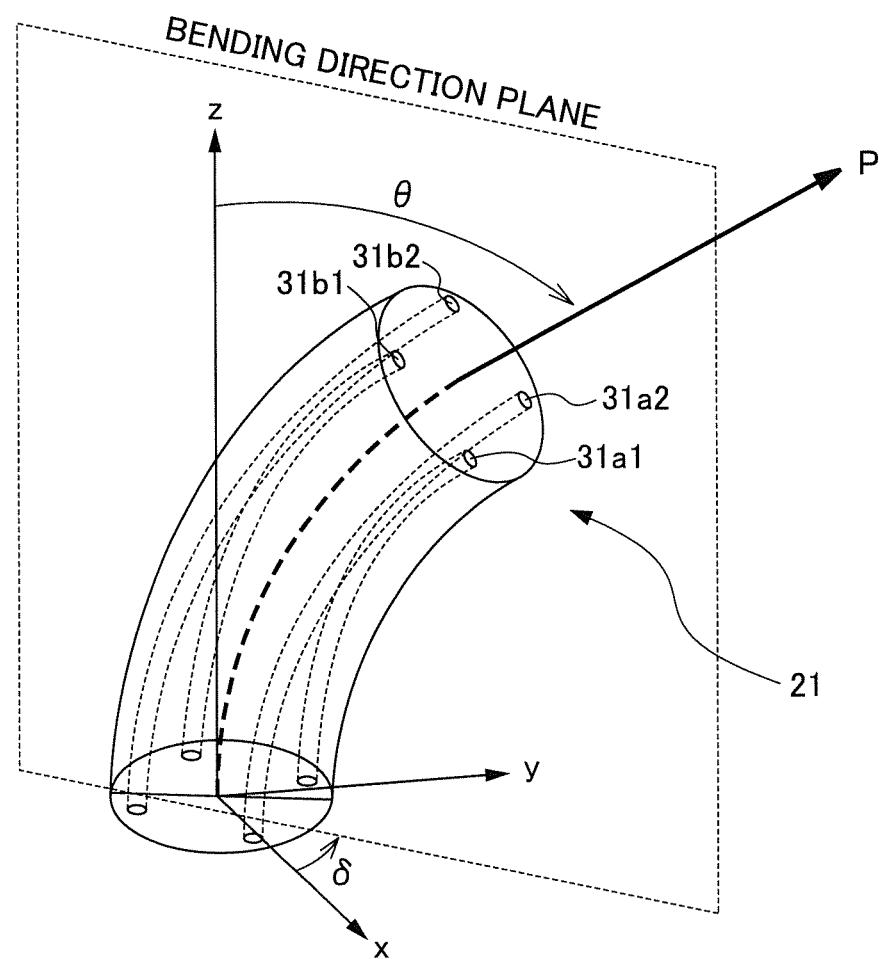
FIG. 3 is a diagram for describing a posture of a forceps tip unit of the forceps manipulator of FIG. 2.

The forceps tip unit 21 has a clamping section for clamping threads or the like used in a surgical operation (clamping section 33 in FIGS. 4A and 4B) and is configured to bend with two degrees of freedom as illustrated in FIG. 3. FIG. 3 is a diagram for describing a posture of the forceps tip unit 21. As illustrated in FIG. 3, a center point of a predetermined cross section of the forceps tip unit 21 (for example, a cross section on the end connected to the drive transmitting unit 23) is set as an origin, an x-axis and a y-axis perpendicular to each other are defined on a two-dimensional plane including this cross section, and a z-axis normal to this cross section is defined, so that a three-dimensional cartesian coordinates system is established. Here, a predetermined plane including an arbitrary straight line on a two-dimensional plane defined by the x-axis and the y-axis and the z-axis will be referred to as a "bending direction plane." A line normal to the cross section of the forceps side of the forceps tip unit 21 will be denoted by "P," and an angle θ between the normal line P and the z-axis will be referred to as a "bending angle θ." That is, the bending angle θ is an index indicating how much the forceps tip unit 21 bends. An angle δ of the bending direction plane rotated from the x-axis as a starting point on the two-dimensional plane defined by the x-axis and the y-axis, that is, an angle δ between the x-axis and the bending direction plane will be hereinafter referred to as a "bending direction δ". That is, the bending direction δ is an index indicating which direction the forceps tip unit 21 bends. The forceps tip unit 21 can bend with two degrees of freedom including the bending direction δ and the bending angle θ.

Here, as illustrated in FIG. 3, four wires 31a1, 31a2, 31b1, and 31b2 are fastened to the forceps tip unit 21. Here, a set of wires 31a1 and 31a2 will be hereinafter referred to as a "wire group 31a." A set of wires 31b1 and 31b2 will be hereinafter referred to as a "wire group 31b."

Figure 4A:
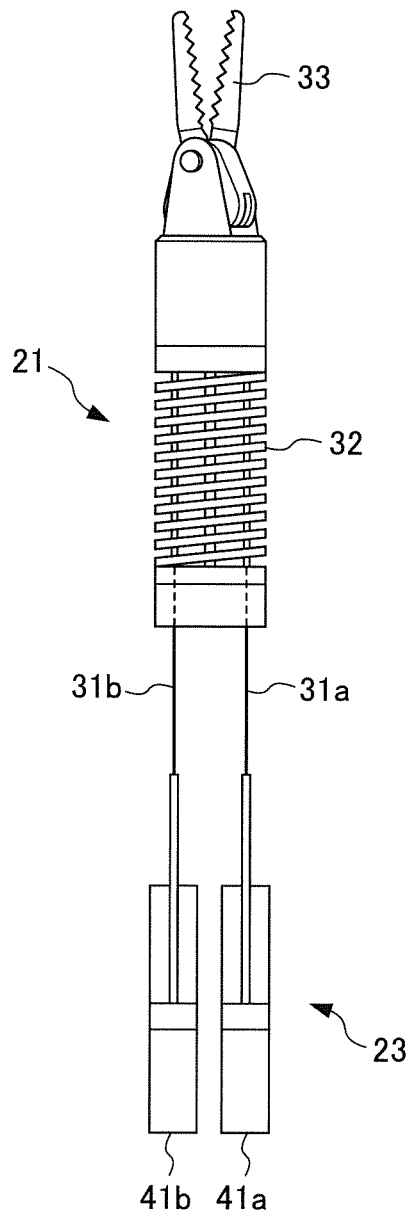
FIGS. 4A and 4B are diagrams illustrating an overview of a principle for driving the forceps tip unit of FIG. 2.
Figure 4B:
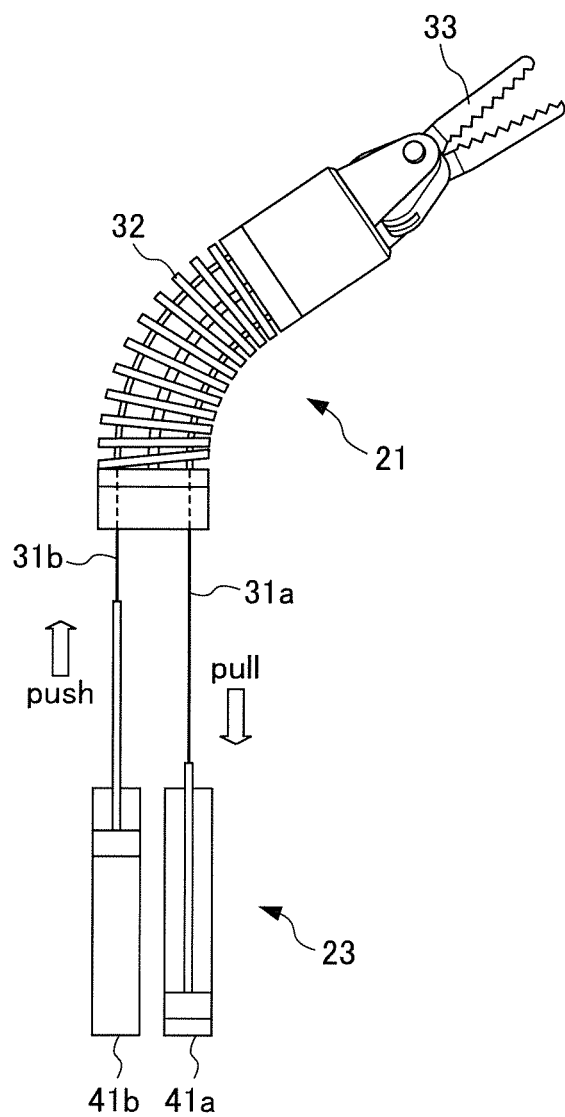

FIGS. 4A and 4B are diagrams illustrating an overview of a principle for driving the forceps tip unit 21.

A tip end side of the wire group 31a is buried in a flexible joint 32 and is fastened to the clamping section 33, and its basal end side (root) is fastened to the pneumatic cylinder group 41a. Here, the pneumatic cylinder group 41a includes two pneumatic cylinders. That is, each of the two of pneumatic cylinders included in the pneumatic cylinder group 41a is fastened to each of the wires 31a1 and 31a2 of the wire group 31a.

Meanwhile, a tip end side of the wire group 31b is buried in the flexible joint 32 and is fastened to the clamping section 33, and its basal end side (root) is fastened to the pneumatic cylinder group 41b. Here, the pneumatic cylinder group 41b includes two pneumatic cylinders. That is, each of the two pneumatic cylinders included in the pneumatic cylinder group 41b is fastened to each of the wires 31b1 and 31b2 of the wire group 31b.

Note that, although not shown in FIGS. 4A and 4B, the pneumatic cylinder groups 41a and 41b constitute a drive unit 22 of FIG. 2. In addition, a part of the wire groups 31a and 31b under the flexible joint 32 in FIGS. 4A and 4B are embedded in the rod-shaped drive transmitting unit 23.

As illustrated in FIGS. 4A and 4B, the forceps tip unit 21 is driven as each of the wire groups 31a and 31b is pushed or pulled by driving each of the pneumatic cylinder groups 41a and 41b. FIG. 4A illustrates the forceps tip unit 21 having a default state before driving. FIG. 4B illustrates the forceps tip unit 21 bending to the right from the default state of FIG. 4A. That is, the right wire group 31a is pulled by the pneumatic cylinder group 41a, and the left wire group 31b is pushed by the pneumatic cylinder group 41b, so that a posture of the forceps tip unit 21 changes from the state of FIG. 4A to the state of FIG. 4B.

Figure 5:
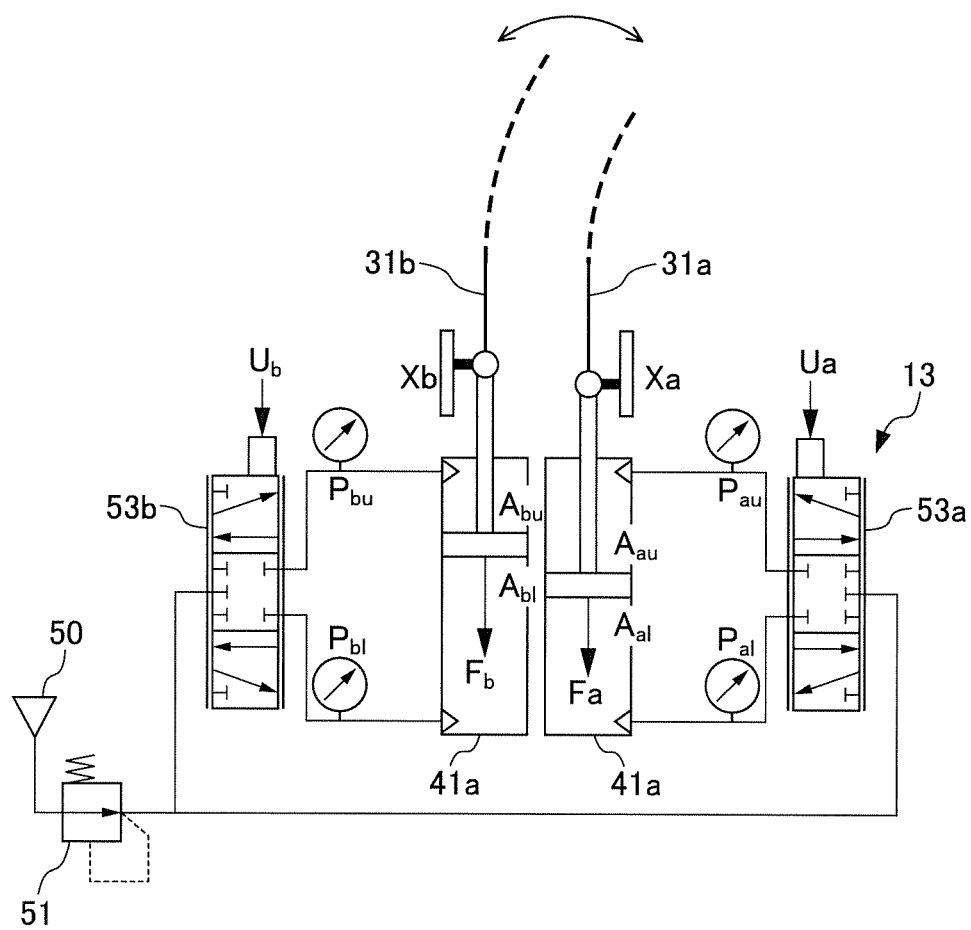
FIG. 5 is a diagram illustrating an overview of a pneumatic system for manipulating the forceps manipulator of the forceps system of FIG. 1.

FIG. 5 is a diagram schematically illustrating a pneumatic system for manipulating the forceps manipulator 11. In the pneumatic system, a plurality of five port type servo valves are connected to the pneumatic pressure supply source 50 such as a compressor through a pressure regulator valve 51. Each servo valve is provided for each of the pneumatic cylinders described above. In the example of FIG. 5, a servo valve group 53a corresponding to the pneumatic cylinder group 41a and a servo valve group 53b corresponding to the pneumatic cylinder group 41b are illustrated to match the example of FIGS. 4A and 4B. As each of the input voltages ua and ub that changes depending on a bending target (bending target gref in FIGS. 7 and 8 described below) of the forceps tip unit 21 (in FIGS. 4A and 4B and the like) is applied to each of the servo valve groups 53a and 53b, a manipulation of each supply pressure Pa and Pb is controlled. As a result, each of the pneumatic cylinder groups 41a and 41b is driven. That is, driving forces of the pneumatic cylinder groups 41a and 41b necessary to bend the forceps tip unit 21 (in FIGS. 4A and 4B and the like) are generated.

In this manner, the bending operation of the forceps tip unit 21 (in FIGS. 4A and 4B and the like) is realized by antagonistic driving using the pneumatic cylinder groups 41a and 41b and the wire groups 31a and 31b arranged in the root of the forceps tip unit 21.

Figure 6A:
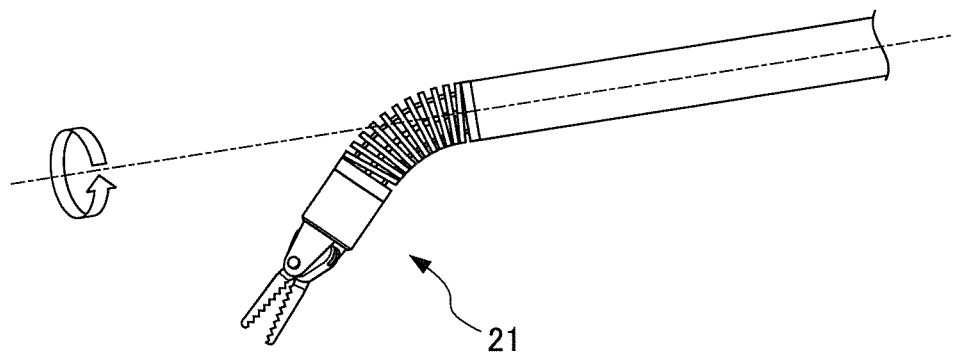
FIGS. 6A and 6B are diagrams for schematically describing a difference in operation between the forceps tip unit of the forceps system of FIG. 1 and the forceps of the related art.
Figure 6B:
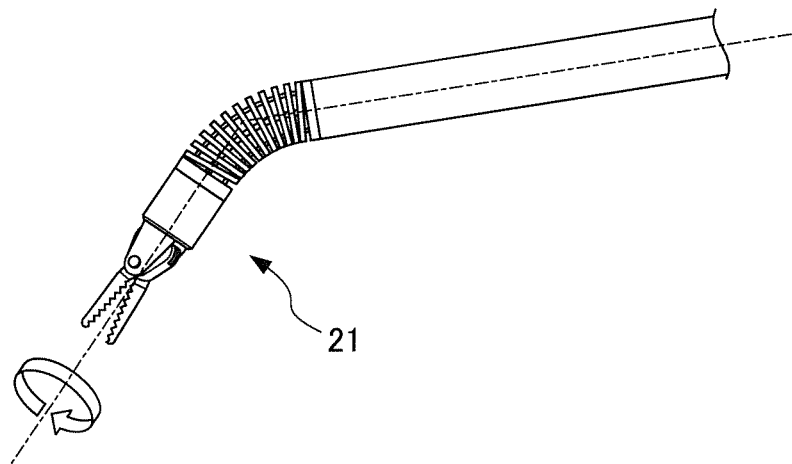

Here, the forceps system 1 according to this embodiment is used to, for example, hold organs by bending the clamping section 33 (FIGS. 4A and 4B) of the forceps tip unit 21 inside a human body as a tool for assisting a manipulation of the laparoscopic surgical operation. FIGS. 6A and 6B are diagrams schematically illustrating a difference in operation between the forceps tip unit 21 of the forceps system 1 according to this embodiment and the forceps of the related art. Specifically, FIG. 6A is a diagram schematically illustrating an operation of the forceps tip unit 21 of the forceps of the related art. FIG. 6B is a diagram schematically illustrating an operation of the forceps tip unit 21 of the forceps system 1 according to this embodiment.

As illustrated in FIG. 6A, in the case of the forceps of the related art, if an operator rotates his/her wrist while bending the forceps tip unit 21, a rotational motion is generated with the forceps being the axis of rotation (corresponding to the axis of the drive transmitting unit 23 of FIG. 2 in this embodiment). Considering an operator's work for inserting a needle or the like using the forceps, a rotational motion is preferably made with the forceps tip unit 21 being the axis of rotation as illustrated in FIG. 6B. For this reason, the forceps in which the forceps tip unit 21 is rotated have been existed in the related art. However, in such forceps of the related art, an operator is required to perform another manipulation such as turning a separate dial by releasing a hand from the operation unit (corresponding to the operation unit 25 or the holding section 26 of FIG. 2) of the forceps once. This manipulation is far from an intuitive operation for an operator. Therefore, an intuitive operation is desirable. In the forceps of the related art, it is difficult to perform a continuous operation such as rotation with respect to the tip while changing the bending direction of the forceps tip unit 21.

In this regard, in the forceps system 1 according to this embodiment, even when an operator rotates his/her wrist (rotation with respect to the drive transmitting unit 23 indicated by the rotation angle α in FIG. 2) without releasing a hand from the operation unit 25 or the holding section 26 (FIG. 2), rotation can be realized with the forceps tip unit 21 being the axis of rotation as illustrated in FIG. 6B.

Specifically, an operator instructs a posture of the forceps tip unit 21 by manipulating the operation unit 25. Therefore, when the bending direction δ and the bending angle θ of the forceps tip unit 21 change in response to an operator's instruction using the operation unit 25, the forceps system 1 can realize rotational motion with the forceps tip unit 21 being the axis of rotation as illustrated in FIG. 6B as seen from the operator. However, if the operator rotates his/her wrist while holding the holding section 26, assuming that the posture control of the forceps tip unit 21 is not performed, the bending direction δ of the forceps tip unit 21 does not follow the operator's instruction using the operation unit 25, but changes by the wrist rotation angle α. That is, the rotation with the forceps tip unit 21 being the axis of rotation illustrated in FIG. 6B becomes impossible (rotation of FIG. 6(A)). In this regard, in the forceps system 1 according to this embodiment, antagonistic driving using the wire groups 31a and 31b and the pneumatic cylinder groups 41a and 41b arranged in the root of the forceps tip unit 21 is controlled such that rotation by the wrist rotation angle α is removed in the bending direction δ of the forceps tip unit 21. Here, in order to perform this control, it is necessary to detect a rotation angle α of the operator's wrist. In this regard, according to this embodiment, in order to detect this rotation angle α, a sensor section 24 having an acceleration sensor and/or a gyro sensor is provided in the forceps manipulator 11. Through this control, changes in the bending direction δ and the bending angle θ of the forceps tip unit 21 follow the operator's instruction with the operation unit 25. As a result, this realizes rotational motion with the forceps tip unit 21 being the axis of rotation as illustrated in FIG. 6B as seen from the operator. As a result, an intuitive operation of an operator is realized. Therefore, the surgery time or the like are expected to be reduced.

Here, in order to perform the posture control of the forceps tip unit 21 (control of the bending operation), a position sensor for detecting a current posture of the forceps tip unit 21 (current values of the bending direction δ and the bending angle θ) may be provided in the forceps manipulator 11. However, since the forceps system 1 according to this embodiment is a pneumatic driving system, a pressure sensor is mounted in the valve box 13. In this regard, according to this embodiment, a relationship between the bending angle θ and the bending direction δ of the forceps tip unit 21 and the supply pressure is obtained experimentally in advance, and a relational expression between the bending angle θ, the bending direction δ, and the supply pressure is established, so that this relational expression is stored in the control unit 12. The control unit 12 performs control based on this relational expression to realize the posture control (control for the bending operation) of the forceps tip unit 21 without providing a position sensor in the forceps manipulator 11.

Figure 7:
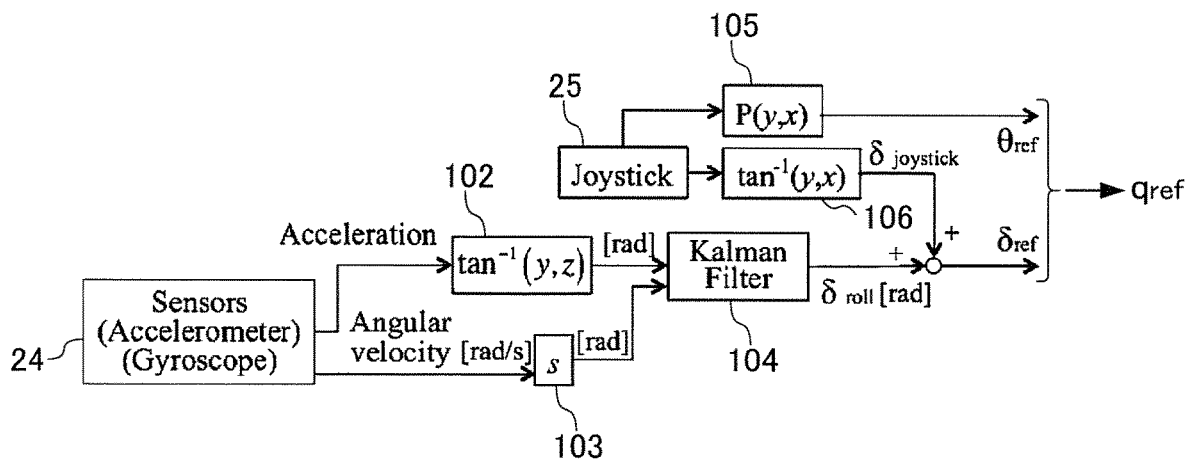
FIG. 7 is a block diagram illustrating an operation unit and a sensor section in posture control of the forceps tip unit of the forceps system of FIG. 1.
Figure 8:
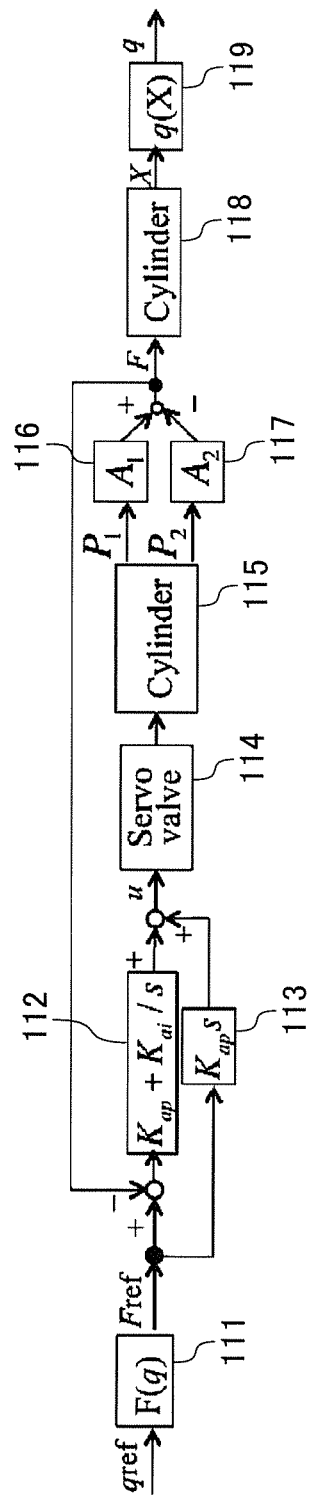
FIG. 8 is a block diagram illustrating a drive unit in posture control of the forceps tip unit of the forceps system of FIG. 1.

The posture control of the forceps tip unit 21 in the forceps system 1 according to this embodiment will now be described in details. FIG. 7 is a block diagram illustrating the operation unit and the sensor section in the posture control of the forceps tip unit 21 of the forceps system 1 according to this embodiment. FIG. 8 is a block diagram illustrating the drive unit in the posture control of the forceps tip unit 21 of the forceps system 1 according to this embodiment.

Here, the operation unit 25 according to this embodiment includes a joystick. Therefore, an operator can tilt the operation unit 25 by a predetermined angle in a predetermined direction by manipulating the operation unit 25. In this regard, it is assumed that the operator instructs the bending direction δ of the forceps tip unit 21 using the tilt direction of the operation unit 25 and instructs the bending angle θ of the forceps tip unit 21 using the tilt angle of the operation unit 25. Note that, although a joystick is employed as the operation unit 25 in this embodiment, any manipulation tool may be employed without a limitation as long as it is arranged in the drive unit 22 side as seen from the drive transmitting unit 23 and can be used to instruct the bending direction δ and the bending angle θ in response to an operator's manipulation.

In FIG. 7, in the block 105, the control unit 12 obtains the tilt angle of the operation unit 25 on the basis of a manipulation signal P(y, x) of the operation unit 25 and outputs it as a bending angle θ_ref instructed from the operator. The bending angle θ_ref instructed from the operator is directly applied as a target bending angle θ_ref of the forceps tip unit 21.

Meanwhile, in the block 106, the control unit 12 obtains a tilt direction of the operation unit 25 on the basis of $\tan^{-1}(y, x)$ of the manipulation signal of the operation unit 25 and outputs it as the bending direction δ_Joystick instructed from the operator. In addition, the control unit 12 obtains the target bending direction δ_ref of the forceps tip unit 21 by adding a rotation angle δ_roll of the operator's arm (corresponding to the rotation angle α of FIG. 2 described above) with respect to the bending direction δ_Joystick instructed from the operator. That is, the control unit 12 realizes the control such that the bending direction δ_Joystick instructed from the operator is not simply set as the target bending direction δ_ref, but the target bending direction δ_ref is set by adding the rotation angle δ_roll of the operator's arm to the bending direction δ_Joystick instructed from the operator.

Note that the control unit 12 calculates the rotation angle δ_roll of the operator's arm in the following way. That is, in the block 102, the control unit 12 outputs a value obtained by applying $\tan^{-1}(y, z)$ to a detection signal of the acceleration sensor of the sensor section 24 as an observation value. In the block 103, the control unit 12 outputs a value obtained by integrating the detection signal of the acceleration sensor of the sensor section 24 as a preliminary estimation value. In addition, in the block 104, the control unit 12 calculates the rotation angle δ_roll of the operator's arm using the Kalman filter by inputting the observation value and the preliminary estimation value.

The target bending angle θ_ref and the target bending direction δ_ref of the forceps tip unit 21 calculated on the basis of the block diagram of FIG. 7 in this manner are input as a target value q_ref of the forceps tip unit 21 in the block diagram of FIG. 8. Here, as described above, according to this embodiment, since a position sensor is not provided in the forceps manipulator 11, a relational expression F(q) between the bending value q of the forceps tip unit 21 and the cylinder driving force F is prepared in advance. In this regard, in the block 111, the control unit 12 computes the relational expression F(q) by using the target value q_ref of the forceps tip unit 21 as an input value and outputs its result as a target driving force F_ref of each pneumatic cylinder (each pneumatic cylinder of the pneumatic cylinder groups 41a and 41b of FIGS. 4A and 4B).

The control unit 12 inputs a difference between this target driving force F-_ref and the cylinder driving force (actual value) obtained from the detection value of the pressure sensor of the valve box 13 (differential pressure between each pneumatic cylinder) to the control block 112 as a control error. In the control block 112, the control unit 12 executes a PI control using this input value to determine an input voltage u of the servo valve of the valve box 13. In addition, in the block 113, the control unit 12 performs feed-forward compensation for the differential value in order to improve a responsiveness to an abrupt change of the target driving force F_ref. That is, the input voltage u subjected to the feed-forward compensation is applied to each servo valve (in the example of FIG. 5, the servo valve group 53a corresponding to the pneumatic cylinder group 41a and the servo valve group 53b corresponding to the pneumatic cylinder group 41b). That is, in FIG. 8, the block 114 represents each servo valve.

In the block 115, the air supplied from each servo valve generates a differential pressure P in each pneumatic cylinder. This differential pressure P generates the cylinder driving force in the blocks 116 and 117. Specifically, the output of the block 116 is the cylinder driving force of the pneumatic cylinder group 41a, and the output of the block 117 is the cylinder driving force of the pneumatic cylinder group. That is, a difference between the output of the block 116 and the output of the block 117 is transmitted to the block 118 as a cylinder driving force caused by antagonistic driving using the pneumatic cylinder groups 41a and 41b.

The block 118 represents each cylinder that generates a displacement by receiving the cylinder driving force. That is, the block 118 receives the cylinder driving force and outputs the displacement of each cylinder. The block 119 represents the forceps tip unit 21 having a posture (including the bending direction δ and the bending angle θ) that changes depending on the cylinder displacement output from the block 118. That is, the block 119 receives the cylinder displacement and outputs an actual value q of the posture of the forceps tip unit 21.

Note that the present invention is not limited to this embodiment, but may encompass modifications, improvements, and the like within a range that the object of the invention can be achieved.

In other words, the forceps system according to the invention may include at least the following configuration and may be embodied in various forms as long as it includes the forceps system 1 of FIG. 1. That is, the forceps system according to the invention (for example, the forceps system 1 of FIG. 1) includes:

a forceps manipulator (for example, the forceps manipulator 11 of FIG. 1 or 2) having:
  a forceps tip unit (for example, the forceps tip unit 21 of FIG. 2) capable of bending with two degrees of freedom including a bending direction and a bending angle;
  a drive unit (for example, the drive unit 22 of FIG. 2) that generates a driving force for the forceps tip unit;
  a drive transmitting unit (for example, the drive transmitting unit 23 of FIG. 2) that transmits the driving force to the forceps tip unit;
an operation unit (for example, the operation unit 25 of FIG. 2) arranged at the drive unit as seen from the drive transmitting unit to instruct the bending direction and the bending angle in response to an operator's manipulation, and
a first detection unit (for example, the sensor section 24 of FIG. 2) that detects an angle of the rotation direction with respect to an axis of the drive transmitting unit; and
a control unit (for example, the control unit 12 of FIG. 1) that controls the drive unit such that the forceps tip unit bends depending on a predetermined target bending direction and a predetermined target bending angle,
wherein the control unit sets the bending angle instructed from the operation unit as a target bending angle, and
the control unit sets a target bending direction on the basis of the bending direction instructed from the operation unit and the angle detected by the first detection unit.

For example, the control unit sets the target bending direction by adding the bending direction and the angle detected by the first detection unit, so that the control described above with reference to FIG. 7 or 8 can be realized. That is, the forceps system may control the posture of the forceps tip unit such that rotation of the angle (the angle detected by the first detection unit) corresponding to the rotation angle of the operator's wrist is removed with respect to the bending direction of the forceps tip unit 21. In this manner, even when the operator's wrist rotates (even when there is a rotation with the drive transmitting unit or the like being the axis of rotation), a change in the bending direction and the bending angle of the forceps tip unit follows the instruction from the operator using the operation unit. Therefore, a rotational motion can be realized with the forceps tip unit being the axis of rotation as seen from the operator (refer to FIG. 6B). As a result, a more intuitive operation is realized for an operator. Therefore, it is possible to anticipate reduction of the surgery time and the like.

Figure 9:
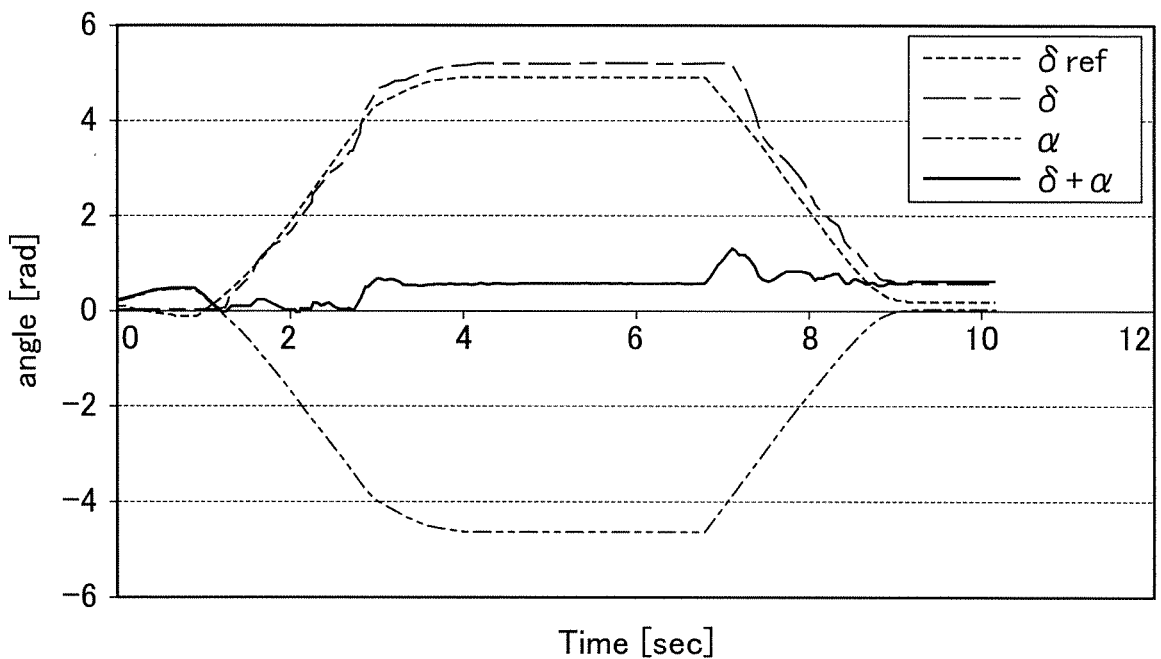
FIG. 9 is a diagram illustrating an effect based on an operational experiment of the forceps system of FIG. 1.

FIG. 9 is a diagram illustrating an effect based on an operational experiment of the forceps system according to the invention. The operational experiment of FIG. 9 is an experiment for checking whether or not the bending direction δ of the forceps tip unit 21 changes depending on the rotation angle α (whether or not the control is performed) when the forceps system 1 of FIG. 1 described above is employed and is rotated at a constant speed with respect to the axis of the drive transmitting unit 23 of the forceps manipulator 11. In this operational experiment, the rotation speed was set to 0.89 [rad/s], and the target bending angle θref as an initial value of the forceps tip unit 21 was set to 0.7 [rad]. In addition, the target bending direction δref was set to 0.0 [rad]. In FIG. 9, a two-dotted chain line indicates the rotation angle α, a dotted line indicates the target bending direction δref, and a one-dotted chain line indicates the actual value of the bending direction δ. A value δ+α obtained by adding the rotation angle α and the actual value δ of the bending direction obtained by detecting the rotation angle α and responding to a change of the target bending direction δref is indicated by a solid line. Focusing on the value δ+α indicated by the solid line, a value around 0.0 [rad] which is the initial value of the bending direction δ is continuously maintained. From this value, it is found that control based on the rotation angle α detected by the sensor section 24 (FIG. 2) is realized, and rotation with respect to forceps tip unit 21 (refer to FIG. 6B) is realized.

Figure 10:
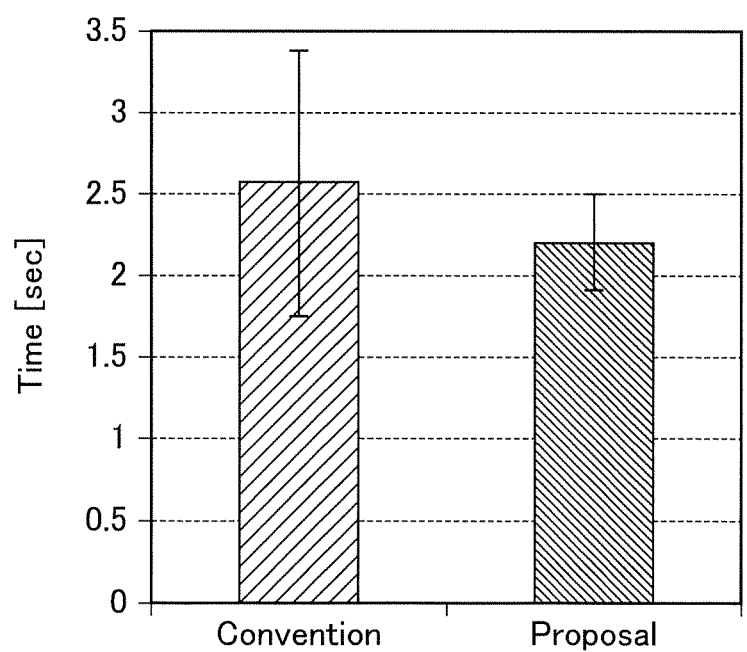
FIG. 10 is a diagram illustrating an effect based on an evaluation experiment of the forceps system of FIG. 1.

FIG. 10 is a diagram illustrating an effect based on an evaluation experiment of the forceps system according to the invention. In the evaluation experiment of FIG. 10, a fully experienced operator performed a task for inserting a needle into a determined position of a biosheet eight times using the forceps of the related art and the forceps system 1 of FIG. 1 according to the invention, and its average time was measured. In FIG. 10, "Convention" indicates the forceps of the related art, and "Proposal" indicates the forceps system 1 of FIG. 1 according to the invention described above. As illustrated in FIG. 10, it was found that, within a risk range of 5%, the forceps system 1 of FIG. 1 according to the invention described above is shown to be more advantageous than the forceps of the related art.

As described above, through two experiments of FIGS. 9 and 10, it was found that, using the forceps system according to the invention, rotation can be made with the forceps tip unit 21 being the axis of rotation (refer to FIG. 6B), and the work time can be reduced due to improvement in forceps manipulability.

In addition, the forceps system further includes a second detection unit (for example, a pressure sensor (not shown) embedded in the valve box 13 of FIG. 1) that detects an actual value of the driving force, wherein the drive unit generates the driving force with a pneumatic pressure, the control unit may store, in advance, a relationship between the bending direction and the bending angle of the forceps tip unit and the driving force for the forceps tip unit, the control unit may obtain a target value of the driving force from the target bending direction and the target bending angle on the basis of the relationship, and the control unit may control the drive unit on the basis of the target value of the driving force and the actual value of the driving force detected by the second detection unit.

As a result, it is possible to estimate the bending direction and the bending angle of the forceps tip unit from the actual value of the driving force of the forceps tip unit (differential pressure of the pneumatic cylinder in the aforementioned embodiment) on the basis of the relationship between the bending direction and the bending angle of the forceps tip unit and the driving force for the forceps tip unit. As a result, any electric sensor is not necessary from the drive unit to the forceps tip unit. As a result, it is possible to facilitate sterilization and washing of the drive unit to the forceps tip unit.

In addition, the forceps tip unit, the drive transmitting unit, and the drive unit may be configured so as to be detachable from the forceps manipulator. As a result, it is possible to further facilitate sterilization and washing of the forceps manipulator and achieve an excellent effect in maintenance.

For example, during a laparoscopic surgical operation, it is required to perform a complicated work using the tip of the forceps. The forceps tip unit has a flexible joint (for example, the flexible joint 32 of FIGS. 4A and 4B) bendable with two degrees of freedom including the bending direction and the bending angle. As a result, it is possible to improve manipulability of the forceps tip unit and easily perform a complicated work.

However, a series of processes according to the invention for realizing the posture control of the forceps tip unit of the forceps manipulator may be executed either on a software basis or on a hardware basis.

In a case where a series of processes are executed on a software basis, a program of this software may be installed in a computer or the like via a network or from a recording medium. The computer may be a computer embedded with a dedicated hardware component or a computer capable of executing various functions by installing various programs, such as a general-purpose personal computer.

A recording medium recorded with various programs for executing a series of processes according to the invention may be a removable medium distributed to provide a user with the program separately from a main body of an information processing device, or a recording medium embedded in advance in the main body of the information processing device. The removable medium includes, for example, a magnetic disk (such as a floppy disk), an optical disk, a magneto optical disk, or the like. The recording medium embedded in the main body in advance may include, for example, ROM that stores the program, a hard disk, or the like.

Note that, in this specification, the step of describing a program stored in the recording medium includes a process sequentially executed in a chronological order or a process executed individually or in parallel but not processed in a chronological order Herein, the system refers to a plurality of devices or the entire device including the processing unit.

EXPLANATION OF REFERENCE NUMERALS 1 forceps system
11 forceps manipulator
12 control unit
13 valve box
14 pneumatic pipe
21 forceps tip unit
22 drive unit
23 drive unit
24 sensor section
25 operation unit
26 holding section
31a1 wire
31a2 wire
31b1 wire
31b2 wire
31a wire group
31b wire group
32 flexible joint
33 clamping section
41a pneumatic cylinder group
41b pneumatic cylinder group
50 pneumatic pressure supply source
51 pressure regulator valve

The invention claimed is:
1. A forceps system comprising:
a forceps manipulator having:
a forceps tip unit capable of bending with two degrees of freedom including a bending direction and a bending angle;
a drive unit that generates a driving force for the forceps tip unit;
a rod-shaped drive transmitting unit that transmits the driving force to the forceps tip unit;
an operation unit arranged at the drive unit which is provided with a proximal end of the drive transmitting unit, to instruct the bending direction and the bending angle in response to an operator's manipulation;

a first detection unit that detects an angle in a rotation direction with respect to an axis of the drive transmitting unit; and a control unit that controls the drive unit such that the forceps tip unit bends depending on a predetermined target bending direction and a predetermined target bending angle, wherein the control unit sets the bending angle instructed from the operation unit as a target bending angle, and the control unit sets a target bending direction on the basis of the bending direction instructed from the operation unit and the angle detected by the first detection unit.

2. The forceps system according to claim 1, further comprising a second detection unit that detects an actual value of the driving force, wherein the drive unit generates the driving force with a pneumatic pressure, the control unit stores, in advance, a relationship between the bending direction and the bending angle of the forceps tip unit and the driving force of the forceps tip unit, the control unit obtains a target value of the driving force from the target bending direction and the target bending angle on the basis of the relationship, and the control unit controls the drive unit on the basis of the target value of the driving force and an actual value of the driving force detected by the second detection unit.

3. The forceps system according to claim 1, wherein the forceps tip unit, the drive transmitting unit, and the drive unit are configured so as to be detachable from the forceps manipulator.

4. The forceps system according to claim 1, wherein the forceps tip unit has a flexible joint capable of bending with two degrees of freedom including the bending direction and the bending angle.

* * * * *